US006211135B1

(12) United States Patent
Miller et al.

(10) Patent No.: US 6,211,135 B1
(45) Date of Patent: Apr. 3, 2001

(54) PROCESSES FOR THE PURIFICATION AND USE OF 2,2-DICHLORO-1,1,1,3,3,3-HEXAFLUOROPROPANE AND AZEOTROPES THEREOF WITH HF

(75) Inventors: Ralph Newton Miller, Newark; V. N. Mallikarjuna Rao; Steven H. Swearingen, both of Wilmington, all of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/283,448

(22) Filed: Apr. 1, 1999

Related U.S. Application Data
(60) Provisional application No. 60/080,710, filed on Apr. 3, 1998.

(51) Int. Cl.$^7$ .................................................. C11D 3/44
(52) U.S. Cl. ........................... 510/408; 510/407; 510/338
(58) Field of Search .................................... 570/124, 134, 570/156, 157, 176; 510/408, 410, 411, 412; 252/67

(56) References Cited

U.S. PATENT DOCUMENTS

| | | | |
|---|---|---|---|
| 4,911,792 | * | 3/1990 | Manzer et al. . |
| 5,057,634 | | 10/1991 | Webster et al. . |
| 5,068,472 | * | 11/1991 | Webster et al. . |

FOREIGN PATENT DOCUMENTS

| | | | |
|---|---|---|---|
| 0542290A1 | * | 11/1992 | (DE) . |
| 0434408 | * | 12/1990 | (EP) . |
| 0 434 408 A1 | | 6/1991 | (EP) ............................. C07C/21/18 |
| 0 736 508 A1 | | 10/1996 | (EP) ............................. C07C/19/10 |
| 0509449A2 | * | 4/1992 | (JP) . |

(List continued on next page.)

Primary Examiner—Yogendra Gupta
Assistant Examiner—Gregory Webb

(57) ABSTRACT

A process is disclosed for the separation of a mixture of HF and $CF_3CCl_2CF_3$. The process involves placing the mixture in a separation zone at a temperature of from about 0° C. to about 100° C. and at a pressure sufficient to maintain the mixture in the liquid phase, whereby an organic-enriched phase comprising less than 69 mole percent HF is formed as the bottom layer and an HF-enriched phase comprising more than 90 mole percent HF is formed as the top layer. The organic-enriched phase can be withdrawn from the bottom of the separation zone and subjected to distillation in a distillation column to recover essentially pure $CF_3CCl_2CF_3$. The distillate comprising HF and $CF_3CCl_2CF_3$ can be removed from the top of the distillation column, while essentially pure $CF_3CCl_2CF_3$ can be recovered from the bottom of the distillation column. Also, the HF-enriched phase can be withdrawn from the top of the separation zone and subjected to distillation in a distillation column. The distillate comprising HF and $CF_3CCl_2CF_3$ can be removed from the top of the distillation column while essentially pure HF can be recovered from the bottom of the distillation column. If desired, the two distillates can be recycled to the separation zone.

Also disclosed are compositions of hydrogen fluoride in combination with an effective amount of $CF_3CCl_2CF_3$ to form an azeotrope or azeotrope-like composition with hydrogen fluoride. Included are compositions containing from about 13.8 to 31.3 mole percent $CF_3CCl_2CF_3$.

Also disclosed is a process for producing 1,1,1,3,3,3-hexafluoropropane from a mixture comprising HF and $CF_3CCl_2CF_3$. This process is characterized by preparing essentially pure $CF_3CCl_2CF_3$ as indicated above, and reacting the $CF_3CCl_2CF_3$ with hydrogen. Another process for producing 1,1,1,3,3,3-hexafluoropropane disclosed herein is characterized by contacting an azeotrope of $CF_3CCl_2CF_3$ as indicated above with hydrogen and reacting the $CF_3CCl_2CF_3$ with hydrogen in the presence of HF.

11 Claims, 1 Drawing Sheet

U.S. PATENT DOCUMENTS 5,171,901 * 12/1992 Gassen et al. .
5,220,083 * 6/1993 Webster et al. .
5,364,992 * 11/1994 Manogue et al. .
5,481,051 * 1/1996 Rao .
5,902,911 * 5/1999 Rao et al. .
6,127,585 * 10/2000 Duzick et al. .

FOREIGN PATENT DOCUMENTS

05909885 * 4/1992 (FR) .
WO 96/17813 6/1996 (WO) .............................. C07C/17/23
WO9951555 * 10/1999 (WO) .
WO9951556 * 10/1999 (WO) .

* cited by examiner

PROCESSES FOR THE PURIFICATION AND USE OF 2,2-DICHLORO-1,1,1,3,3,3-HEXAFLUOROPROPANE AND AZEOTROPES THEREOF WITH HF

This application claims the priority benefit of U.S. Provisional Application 60/080,710, filed Apr. 3, 1998.

FIELD OF THE INVENTION

This invention relates to the purification of 2,2-dichloro-1,1,1,3,3,3-hexafluoropropane (i.e., $CF_3CCl_2CF_3$, or CFC-216aa), its azeotropic compositions with hydrogen fluoride and their use.

BACKGROUND

CFC-216aa can be used to prepare 1,1,1,3,3,3-hexafluoropropane (i.e., $CF_3CH_2CF_3$ or HFC-236fa) by hydrogenolysis (see e.g., PCT International Publication No. 96/17813). The product, $CF_3CH_2CF_3$, has numerous uses including use as a refrigerant and fire extinguishant.

CFC-216aa can be prepared from an appropriately substituted three-carbon precursor (e.g., perchloropropene) by chlorofluorination. Typically excess HF is used to obtain favorable reaction rates for conversion of the precursors to CFC-216aa. HF may be removed from the halogenated hydrocarbon components of the product mixture using conventional aqueous solution scrubbing techniques. However, the production of substantial amounts of scrubbing discharge can create aqueous waste disposal concerns.

There remains a need for processes that utilize HF in such product mixtures in an environmentally benign manner.

SUMMARY OF THE INVENTION

This invention provides a process for the separation of a mixture comprising HF and $CF_3CCl_2CF_3$. The process comprises placing the mixture in a separation zone at a temperature of from about 0° C. to about 100° C. and at a pressure sufficient to maintain the mixture in the liquid phase, whereby an organic-enriched phase comprising less than 69 mole percent HF is formed as the bottom layer and an HF-enriched phase comprising more than 90 mole percent HF is formed as the top layer.

The organic-enriched phase can be withdrawn from the bottom of the separation zone and subjected to distillation in a distillation column to recover essentially pure $CF_3CCl_2CF_3$. The distillate comprising HF and $CF_3CCl_2CF_3$ can be removed from the top of the distillation column, while $CF_3CCl_2CF_3$ which is essentially free of HF can be recovered from the bottom of the distillation column. If desired, the distillate can be recycled to the separation zone.

The HF-enriched phase can be withdrawn from the top of the separation zone and subjected to distillation in a distillation column. The distillate comprising HF and $CF_3CCl_2CF_3$ can be removed from the top of the distillation column while essentially pure HF can be recovered from the bottom of the distillation column. If desired, the distillate can be recycled to the separation zone.

Also provided are compositions which comprise hydrogen fluoride in combination with an effective amount of $CF_3CCl_2CF_3$ to form an azeotrope or azeotrope-like composition with hydrogen fluoride, said composition containing from about 13.8 to 31.3 mole percent $CF_3CCl_2CF_3$.

Also provided is a process for producing 1,1,1,3,3,3-hexafluoropropane from a mixture comprising HF and $CF_3CCl_2CF_3$. The process is characterized by preparing $CF_3CCl_2CF_3$ which is essentially free of HF as indicated above, and reacting said $CF_3CCl_2CF_3$ with hydrogen.

Also provided is another process for producing 1,1,1,3,3-hexafluoropropane. This process is characterized by contacting an azeotrope of $CF_3CCl_2CF_3$ and HF as described above, with hydrogen, and reacting the $CF_3CCl_2CF_3$ with hydrogen in the presence of HF.

DETAILED DESCRIPTION

Figure 1:
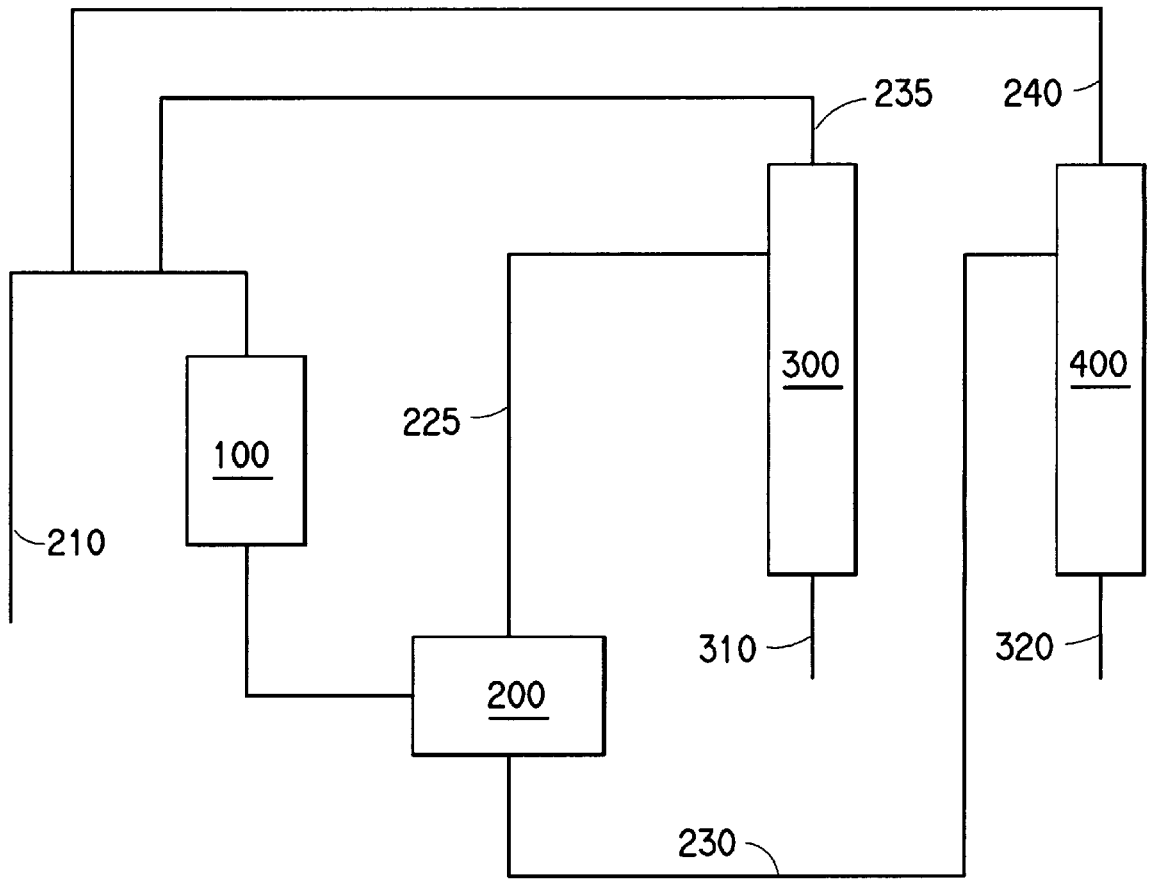
FIG. 1 is a schematic flow diagram of an embodiment of the purification process of this invention, namely an azeotrope separation process.

FIG. 1 is illustrative of one method of practicing a separation process in accordance with this invention. Referring to FIG. 1, a feed mixture comprising HF and CFC-216aa with a HF:CFC-216aa molar ratio of greater than about 1:1, is passed through line (210), along with recycles from lines (235) and (240), through cooler (100) into a separation zone (200). The feed mixture might, for example, be derived from a reactor for synthesizing CFC-216aa by the chlorofluorination of perchloropropene, and feed line (210) might follow an HCl removal column (not shown). The separation zone (200) is held at a temperature of between from about 0° C. and about 100° C., preferably between about 0° C. and 25° C., and at a pressure sufficient to keep the mixture as a liquid. For example, at about 100° C. the separator would be maintained at a pressure greater than about 260 psia (1792 kPa), and at about 0° C. the separator would be maintained at a pressure greater than about 10 psia (69 kPa). At these temperatures, the liquefied stream forms two phases, one phase organic-enriched compared to the feed mixture, the other phase HF-enriched compared to the feed mixture. The organic-rich phase typically contains more than about 31 mole % organic; the HF-rich phase typically contains more than about 90 mole % HF. Within the preferred temperature range of 0° C. to 25° C., the organic-rich phase typically contains 10 mole percent HF, or less, and the HF-rich phase temperature contains 98 mole percent HF, or more.

The HF-rich phase is removed through line (225) from the top of the separation zone (200) and fed to a multiple stage distillation column (300) operated under conditions such that a lower boiling azeotropic or azeotrope-like mixture is formed comprising HF and CFC-216aa. The column (300) operating pressure is typically between from about 10 psia (69 kPa) to about 250 psia (1723 kPa) and the top temperature is typically from about 0° C. to about 100° C., but with the exact temperature being dependent on the operating pressure. The HF/CFC-216aa azeotrope is distilled overhead and removed from the top of the column (300) through line (235) and recycled back to the cooler (100). Essentially pure HF can be removed from the bottom the distillation column though line (310).

The organic-rich phase is removed from the bottom of the separation zone (200) through line (230) and fed to another multistage distillation column (400) operated under conditions such that a low boiling azeotropic or azeotrope-like composition comprising HF and CFC-216aa is formed. The column (400) operating pressure is typically between from about 10 psia (69 kPa) to about 250 psia (1723 kPa) and the top temperature is from between about 0° C. to about 100° C., but with the exact temperature being dependent on the operating pressure. The HF/CFC-216aa azeotrope is distilled overhead and removed from the top of the column through line (240) and recycled to the cooler (100). Essentially pure CFC-216aa is removed from the bottom of the column through line (320).

As noted above, the CFC-216aa may be reacted with hydrogen to form $CF_3CH_2CF_3$. Examples of this process include processes where the CFC-216aa is reacted with hydrogen at an elevated temperature of about 300° C. or less in the presence of a hydrogenation catalyst. Also included are processes where CFC-216aa is reacted with hydrogen without a catalyst at a temperature within the range of about 350° C. to 700° C.

Those skilled in the art will recognize that since the drawings are representational, it will be necessary to include further items of equipment in an actual commercial plant, such as pressure and temperature sensors, pressure relief and control valves, compressors, pumps, storage tanks and the like. The provision of such ancillary items of equipment would be in accordance with conventional chemical engineering practice.

The above embodiment of this invention involves azeotropic distillation of mixtures of HF and $CF_3CCl_2CF_3$ (CFC-216aa). The product mixtures distilled in accordance with this invention can be obtained from a variety of sources. These sources include product mixtures obtained by chlorofluorination of $CF_3CCl=CCl_2$ to $CF_3CCl_2CF_3$.

Of note is a process wherein $CF_3CCl_2CF_3$ is purified from a mixture which consists essentially of hydrogen fluoride in combination with an effective amount of $CF_3CCl_2CF_3$ to form an azeotrope or azeotrope-like composition with hydrogen fluoride, said azeotropic composition containing from about 13.8 to 31.3 mole percent $CF_3CCl_2CF_3$.

The present invention also provides compositions which consist essentially of hydrogen fluoride and an effective amount of $CF_3CCl_2CF_3$ to form an azeotropic combination with hydrogen fluoride. By effective amount is meant an amount which, when combined with HF, results in the formation of an azeotrope or azeotrope-like mixture. As recognized in the art, an azeotrope or an azeotrope-like composition is an admixture of two or more different components which, when in liquid form under given pressure, will boil at a substantially constant temperature, which temperature may be higher or lower than the boiling temperatures of the individual components, and which will provide a vapor composition essentially identical to the liquid composition undergoing boiling.

An azeotrope is a liquid mixture that exhibits a maximum or minimum boiling point relative to the boiling points of surrounding mixture compositions. An azeotrope is homogeneous if only one liquid phase is present. An azeotrope is heterogeneous if more than one liquid phase is present. Regardless, a characteristic of minimum boiling azeotropes is that the bulk liquid composition is then identical to the vapor composition in equilibrium therewith, and distillation of the azeotropic mixture is ineffective as a separation technique. For the purpose of this discussion, azeotrope-like composition means a composition which behaves like an azeotrope (i.e., has constant-boiling characteristics or a tendency not to fractionate upon boiling or evaporation). Thus, the composition of the vapor formed during boiling or evaporation of such compositions is the same as or substantially the same as the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotropic composition may change when the azeotrope or azeotrope-like liquid composition is subjected to boiling at different pressures. Thus an azeotrope or an azeotrope-like composition may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte, Ind. Eng. Chem. Process Des. Dev. 1980, 19, pp 432–439). Experimental identification of azeotropic compositions involving the same components may be used to confirm the accuracy of such calculations and/or to modify the calculations for azeotropic compositions at the same or other temperatures and pressures.

Compositions may be formed which consist essentially of azeotropic combinations of hydrogen fluoride with $CF_3CCl_2CF_3$. These include a composition consisting essentially of from about 86.2 to about 68.7 mole percent HF and from about 13.8 to 31.3 mole percent $CF_3CCl_2CF_3$ (which forms an azeotrope boiling at a temperature from between about 0° C. and about 110° C. and a pressure between about 73.9 kPa and about 2217 kPa).

At atmospheric pressure, the boiling points of hydrofluoric acid and CFC-216aa are about 19.5° C. and 32.6° C., respectively. At a pressure of 12.7 psia (87.7 kPa) and 4° C., the relative volatility was found to be nearly 1.0 as 85.7 mole percent HF and 14.3 mole percent CFC-216aa was approached. At a pressure of 620 kPa (89.9 psia) and 60° C., the relative volatility was found to be nearly 1.0 as 77.4 mole percent HF and 22.6 mole percent CFC-216aa was approached. These data indicate that the use of conventional distillation procedures will not result in the separation of a substantially pure compound because of the low value of relative volatility of the compounds.

To determine the relative volatility of HF with each of CFC-216aa, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, were obtained and analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", 4th Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and CFC-216aa behave in an ideal mainer, and can sufficiently predict the relative volatilities of the components in such mixtures. Thus, while HF has a good relative volatility compared to CFC-216aa at low CFC-216aa concentrations, the relative volatility becomes nearly 1.0 as 22.6 mole percent CFC-216aa was approached at 60° C. This would make it impossible to separate CFC-216aa from HF by conventional distillation from such a mixture. Where the relative volatility approaches 1.0 defines the system as forming a near-azeotrope. Where the relative volatility is 1.0 defines the system as forming an azeotrope.

It has been found that azeotropes of HF and CFC-216aa are formed at a variety of temperatures and pressures. At a pressure of 12.7 psia (87.7 kPa) and 4° C., the azeotrope vapor composition was found to be about 85.7 mole percent HF and about 14.3 mole percent CFC-216aa. At a pressure of 89.9 psia (620 kPa) and 60° C., the azeotrope vapor composition was found to be about 77.4 mole percent HF and about 22.6 mole percent CFC-216aa. Based upon the above findings, it has been calculated that an azeotropic composition of about 86.2 mole percent HF and about 13.8 mole percent CFC-216aa can be formed at 0° C. and 10.7 psia (73.9 kPa) and an azeotropic composition of about 68.7 mole percent HF and about 31.3 mole percent CFC-216aa can be formed at 110° C. and 322 psia (2217 kPa). Accordingly, the present invention provides an azeotrope or azeotrope-like composition consisting essentially of from about 86.2 to 68.7 mole percent HF and from about 13.8 to 31.3 mole percent CFC-216aa, said composition having a boiling point from about 0° C. at 73.9 kPa to about 110° C. at 2217 kPa.

The CFC-216aa/HF azeotrope is useful as recycle to a chlorofluorination reactor, where the recycled HF can function as a reactant and the recycled CFC-216aa can function to moderate the temperature effect of the heat of reaction. The azeotrope can also be use as a starting material for the production of 1,1,1,3,3,3-hexafluoropropane (i.e., $CF_3CH_2CF_3$ or HFC-236fa), 2-chloro-1,1,1,2,3,3,3-heptafluoropropane (i.e., $CF_3CClFCF_3$ or CFC-217ba) and perfluoropropane (i.e., $CF_3CF_2CF_3$ or FC-218). It will also be apparent to one of ordinary skill in the art that distillation including azeotropes with HF can typically be run under more convenient conditions than distillation without HF, e.g., where HF is removed prior to distillation. HF may be removed from the halogenated hydrocarbon components of the product mixture using conventional aqueous solution scrubbing techniques. However, the production of substantial amounts of scrubbing discharge can create aqueous waste disposal concerns.

CFC-216aa (essentially free of HF or as an azeotrope with HF) can be hydrogenolyzed to HFC-236fa either in the presence or the absence of a catalyst. PCT International Publication No. WO 96/17813 discloses a process for the hydrogenolysis of CFC-216aa to HFC-236fa at an elevated temperature of about 300° C. or less in the presence of a catalyst containing a catalytically effective amount of palladium supported on a support selected from the group consisting of fluorinated alumina, aluminum fluoride and mixtures thereof. U.S. Pat. No. 5,364,992 discloses a process for the hydrogenolysis of CFC-216aa to HFC-236fa contacting CFC-216aa with at least 0.1 mole of hydrogen per mole of CFC-216aa in an empty reaction vessel of nickel, iron or their alloys at a pressure within the range of from 0 psig (101 kPa) to 1000 psig (6994 kPa), at a temperature within the range of from 350° C. to 700° C. and for a time sufficient to produce HFC-236fa.

While the initial mixture treated in accordance with the present invention can be obtained from a variety of sources, including by adding CFC-216aa to HF-containing compositions, an advantageous use of the instant invention resides in treating the effluent mixtures from the preparation of CFC-216aa as described above. Generally, the reaction effluents have a molar ratio of HF:CFC-216aa from about 0.1:1 to about 100:1. The preferred HF:CFC-216aa molar ratio is from about 1:1 to 10:1 for vapor phase fluorination reactions and about 1:1 to about 50:1 for liquid phase reactions. The most preferred HF:CFC-216aa molar ratio is from about 2:1 to 5:1 to achieve maximum benefit from the instant process. When the initial mixture treated in accordance with the invention also contains HCl and other low-boilers (e.g., $CF_3CClFCF_3$), the HCl and other low-boilers can be removed in another distillation column before feeding the mixture to the azeotrope separation columns.

High-boilers, if present, can be removed in an independent distillation column after separation of HF from CFC-216aa.

The distillation and separation equipment and its associated feed lines, effluent lines and associated units should be constructed of materials resistant to hydrogen fluoride, hydrogen chloride and chlorine. Typical materials of construction, well-known to the fluorination art, include stainless steels, in particular of the austenitic type, and the well-known high nickel alloys, such as Monel® nickel-copper alloys, Hastelloy® nickel-based alloys and, Inconel® nickel-chromium alloys. Also suitable for reactor fabrication are such polymeric plastics as polytrifluorochloroethylene and polytetrafluoroethylene, generally used as linings.

Without further elaboration, it is believed that one skilled in the art can, using the description herein, utilize the present invention to its fullest extent. The following preferred specific embodiments are, therefore, to be construed as merely illustrative, and does not constrain the remainder of the disclosure in any way whatsoever.

EXAMPLES

| Legend | |
|---|---|
| 113 is $CCl_2FCClF_2$ | 114 is $CClF_2CClF_2$ |
| 115 is $CClF_2CF_3$ | 215aa is $CClF_2Cl_2CF_3$ |
| 215 ca is $CCl_2FCF_2CClF_2$ | 216aa is $CF_3CCl_2CF_3$ |
| 216ba is $CClF_2CClFCF_3$ | 216ca is $CClF_2CF_2CClF_2$ |
| 217ba is $CF_3CClFCF_3$ | 217ca is $CClF_2CF_2CF_3$ |
| 226da is $CF_3CHClCF_3$ | 1213xa is $CCl_2=CClCF_3$ |
| 1214 is $C_3Cl_2F_4$ | 1215 is $C_3ClF_5$ |
| T is temperature | C.T. is contact time |

Example 1

In the following example, all values for the compounds are in moles per unit time and temperatures are in degrees Celsius. The data were obtained by calculation using measured and calculated thermodynamic properties. The numbers at the top of the columns refer to FIG. 1.

Example 1

| Compound | 210 Feed Mixture | 100 Cooler Feed | 200 Decanter Feed | 225 HF-Rich Phase | 230 Organic-Rich Phase |
|---|---|---|---|---|---|
| HF | 60 | 63.2 | 63.2 | 62.9 | 0.35 |
| 216aa | 10 | 10.8 | 10.8 | 0.71 | 10.1 |
| Temp. °C. | 50 | 48.4 | 0 | 0.0 | 0.0 |
| Press. KPa (psia) | 791 (114.7) | 446 (64.7) | 515 (74.7) | 515 (74.7) | 515 (74.7) |

| Compound | 235 HF Col. Dist. | 310 HF Col. Tails | 240 Org. Col. Dist. | 320 Org. Col. Tails |
|---|---|---|---|---|
| HF | | 2.9 | 60 | 0.35 | <0.01 |
| 216aa | | 0.71 | <0.01 | 0.07 | 10.0 |
| Temp. °C. | | 48.3 | 67.7 | 48.4 | 84.6 |
| Press. kPa (psia) | | 446 (64.7) | 460 (66.7) | 446 (64.7) | 460 (66.7) |

Example 2

Chromium oxide (47.25 g, 35 mL, 10–20 mesh, (2.0–0.84 mm)), obtained from the pyrolysis of ammonium dichromate prepared according to the procedure described in U.S. Pat. No. 5,036,036, was placed in a ⅝" (1.58 cm) diameter Inconel® nickel alloy reactor heated in a fluidized sand bath. It was heated to 175° C. in a flow of nitrogen (50 cc/min) at which time HF flow (50 cc/min) was also started through the reactor. After 15 minutes, the nitrogen flow was decreased to 20 cc/min and the HF flow increased to 80 cc/min. The reactor temperature was gradually increased to 400° C. during a 2 hour period and maintained at 400° C. for an additional 30 minutes. At the end of this period the reactor was brought to the desired operating temperature for catalyst evaluation under a nitrogen flow.

The results of the chlorofluorination reaction are shown in Table 2 in area %.

TABLE 2

| T °C. | Molar Ratio HF:1213xa:$Cl_2$ | C.T. Sec. | % 217ba | % 226da | % 216aa | % 216ba | % 215aa | % Others |
|---|---|---|---|---|---|---|---|---|
| 250 | 20:1:2 | 60 | 0.3 | 1.8 | 10.1 | 9.9 | 74.9 | 3.0 |
| 260 | 20:1:2 | 60 | 0.5 | 2.5 | 15.6 | 10.8 | 67.8 | 2.8 |
| 260 | 20:1:4 | 60 | 0.5 | 0.7 | 10.6 | 13.2 | 72.4 | 2.6 |
| 260 | 10:1:2 | 60 | 0.2 | 0.3 | 5.7 | 9.7 | 82.4 | 1.7 |
| 260 | 20:1:4 | 30 | 0.5 | 0.8 | 8.5 | 11.8 | 76.2 | 2.3 |
| 275 | 20:1:2 | 30 | 1.1 | 2.5 | 23.4 | 12.4 | 57.8 | 2.8 |
| 275 | 20:1:2 | 60 | 1.0 | 2.8 | 27.8 | 11.2 | 54.9 | 2.4 |
| 275 | 20:1:4 | 15 | 1.5 | 1.1 | 16.0 | 14.9 | 64.4 | 2.1 |
| 300 | 10:1:2 | 30 | 1.3 | 1.1 | 45.7 | 9.5 | 40.9 | 1.5 |
| 300 | 20:1:2 | 30 | 3.1 | 1.9 | 48.3 | 12.8 | 31.6 | 2.2 |
| 300 | 20:1:2 | 15 | 3.4 | 2.7 | 45.4 | 11.4 | 34.6 | 2.5 |
| 325 | 6:1:2 | 30 | 3.9 | 0.0 | 80.7 | 9.7 | 4.7 | 1.0 |

Others include mostly 1215, as well as 113, 114, 115, 1214, 215ca, 216ca and 217ca.

Example 3

A 15" (381 mm)×⅜" (9.5 mm) O.D. gold-lined Hastelloy C276® nickel alloy U-tube reactor was used for hydrodehalogenation. $CF_3CCl_2CF_3$ and $H_2$ were fed to the reactor at a pressure of 300 psig (2169 kPa) with a molar ratio of $H_2$:$CF_3CCl_2CF_3$ of 6:1. Results (in mole %) of the hydrodehalogenation reaction at various temperatures and contact times are shown in Table 3.

TABLE 3

| Temp. °C. | C.T. (min) | % Conv. 216aa | % Sel. to 236fa | % Sel. To 226da |
|---|---|---|---|---|
| 200 | 1.8 | 1 | 7 | 1 |
| 440 | 1.2 | 34 | 5 | 93 |
| 440 | 2.4 | 61 | 12 | 87 |
| 480 | 0.6 | 57 | 11 | 88 |
| 480 | 1.2 | 92 | 34 | 66 |
| 480 | 2.3 | 94 | 40 | 60 |
| 520 | 0.6 | 95 | 43 | 56 |
| 520 | 1.1 | 99 | 64 | 35 |
| 520 | 2.2 | 100 | 78 | 22 |
| 560 | 0.5 | 100 | 77 | 22 |
| 560 | 1.1 | 100 | 87 | 13 |
| 560 | 2.1 | 100 | 95 | 4 |
| 580 | 1 | 100 | 95 | 5 |
| 590 | 1 | 100 | 97 | 2 |
| 600 | 0.5 | 100 | 95 | 4 |
| 600 | 1 | 100 | 98 | 1 |
| 600 | 2 | 100 | 98 | 0 |

What is claimed is:

1. A composition comprising hydrogen fluoride in combination with an effective amount of $CF_3CCl_2CF_3$ to form an azeotrope or azeotrope-like composition with hydrogen fluoride, said composition containing from about 13.8 to 31.3 mole percent $CF_3CCl_2CF_3$.

2. A process for the separation of a mixture comprising HF and $CF_3CCl_2CF_3$, comprising:

(a) placing the mixture in a separation zone at a temperature of from about 0° C. to about 100° C. and at a pressure sufficient to maintain the mixture in the liquid phase, whereby an organic-enriched phase comprising less than 69 mole percent HF is formed as the bottom layer and an HF-enriched phase comprising more than 90 mole percent HF is formed as the top layer;

(b1) withdrawing the organic-enriched phase from the bottom of the separation zone and distilling it in a distillation column;

(c1) removing a composition of claim 1 as a distillate comprising HF and $CF_3CCl_2CF_3$ from the top of the distillation column of (b1); and (d1) recovering $CF_3CCl_2CF_3$ which is essentially free of HF from the bottom of the distillation column of (b1).

3. The process of claim 2 wherein the separation zone is operated at a temperature of from 0° C. to 25° C.

4. The process of claim 2 wherein the distillate removed in (c1) is recycled to the separation zone.

5. A process for the separation of a mixture comprising HF and $CF_3CCl_2CF_3$, comprising:
- (a) placing the mixture in a separation zone at a temperature of from about 0° C. to about 100° C. and at a pressure sufficient to maintain the mixture in the liquid phase, whereby an organic-enriched phase comprising less than 69 mole percent HF is formed as the bottom layer and an HF-enriched phase comprising more than 90 mole percent HF is formed as the top layer;
- (b2) withdrawing the HF-enriched phase from the top of the separation zone and distilling it in a distillation column;
- (c2) removing a composition of claim 1 as a distillate comprising HF and $CF_3CCl_2CF_3$ from the top of the distillation column of (b2); and
- (d2) recovering essentially pure HF from the bottom of the distillation column of (b2).

6. The process of claim 5 wherein the distillate removed in (c2) is recycled to the separation zone.

7. The process of claim 6 further comprising (b1) withdrawing the organic-enriched phase from the bottom of the separation zone and distilling it in a distillation column; (c1) removing the distillate comprising HF and $CF_3CCl_2CF_3$ from the top of the distillation column of (b1); and (d1) recovering $CF_3CCl_2CF_3$ which is essentially free of HF from the bottom of the distillation column of (b1).

8. A process for producing 1,1,1,3,3,3-hexafluoropropane, characterized by:
- contacting (i) a composition of claim 1 with (ii) hydrogen; and
- reacting the $CF_3CCl_2CF_3$ with hydrogen in the presence of HF.

9. A process for producing 1,1,1,3,3,3-hexafluoropropane from a mixture comprising HF and $CF_3CCl_2CF_3$, characterized by:
- (a) placing the mixture in a separation zone at a temperature of from about 0° C. to about 100° C. and at a pressure sufficient to maintain the mixture in the liquid phase, whereby an organic-enriched phase comprising less than 69 mole percent HF is formed as the bottom layer and an HF-enriched phase comprising more than 90 mole percent HF is formed as the top layer;
- (b1) withdrawing the organic-enriched phase from the bottom of the separation zone and distilling it in a distillation column;
- (c1) removing a composition of claim 1 as a distillate comprising HF and $CF_3CCl_2CF_3$ from the top of the distillation column of (b1);
- (d1) recovering $CF_3CCl_2CF_3$ which is essentially free of HF from the bottom of the distillation column of (b1); and
- (e) reacting said $CF_3CCl_2CF_3$ from (d1) with hydrogen.

10. The composition of claim 1 which is a product of a process comprising
- (a) placing a mixture comprising HF and $CF_3CCl_2CF_3$, in a separation zone at a temperature of from about 0° C. to about 100° C. and at a pressure sufficient to maintain the mixture in the liquid phase, whereby an organic-enriched phase comprising less than 69 mole percent HF is formed as the bottom layer and an HF-enriched phase comprising more than 90 mole percent HF is formed as the top layer;
- (b1) withdrawing the organic-enriched phase from the bottom of the separation zone and distilling it in a distillation column; and
- (c1) removing the composition as a distillate from the top of the distillation column of (b1).

11. The composition of claim 1 which is a product of a process comprising
- (a) placing a mixture comprising HF and $CF_3CCl_2CF_3$, in a separation zone at a temperature of from about 0° C. to about 100° C. and at a pressure sufficient to maintain the mixture in the liquid phase, whereby an organic-enriched phase comprising less than 69 mole percent HF is formed as the bottom layer and an HF-enriched phase comprising more than 90 mole percent HF is formed as the top layer;
- (b2) withdrawing the HF-enriched phase from the top of the separation zone and distilling it in a distillation column; and
- (c2) removing the composition as a distillate from the top of the distillation column of (b2).

* * * * *